United States Patent [19]
Lavimodiere

[11] Patent Number: 5,478,506
[45] Date of Patent: Dec. 26, 1995

[54] KEY-FILL VAPORIZER ADAPTOR WITH OVERFILL PROTECTION

[75] Inventor: Maurice Lavimodiere, Barrie, Canada

[73] Assignee: Southmedic Inc., Barrie, Canada

[21] Appl. No.: 341,649

[22] Filed: Nov. 17, 1994

[51] Int. Cl.⁶ .................................................. A61M 11/00
[52] U.S. Cl. ................... 261/72.1; 261/DIG. 65; 128/203.26; 128/202.27; 128/203.12
[58] Field of Search .................... 128/203.26, 202.27, 128/203.12; 261/72.1, DIG. 65

[56] References Cited

U.S. PATENT DOCUMENTS

| | | | |
|---|---|---|---|
| 4,796,615 | 1/1989 | Bullock et al. | 128/202.27 |
| 4,879,997 | 11/1989 | Bickford | 128/203.12 |
| 4,883,049 | 11/1989 | McDonald | 128/203.12 |
| 5,209,225 | 5/1993 | Glenn | 128/203.12 |
| 5,293,865 | 3/1994 | Altner et al. | 128/203.26 |
| 5,329,939 | 7/1994 | Howe | 128/203.12 |

FOREIGN PATENT DOCUMENTS

2041184  4/1991  Canada .

*Primary Examiner*—Tim R. Miles
*Attorney, Agent, or Firm*—Bauer & Schaffer

[57] ABSTRACT

An apparatus is disclosed for converting vaporizers such as the Drager™ model 19 from pour-fill to safer indexed key-fill, and for providing overfill protection. A hollow screw is screwed up into an existing screw hole underneath the vaporizer that opens into the fluid storage compartment. A banjo encircling the screw provides two channels, one to dispense filling fluid up around the screw and into the vaporizer, and one to carry decompressing air back from the hollow through the screw. Each channel is connected to a separate pipe that communicates with a channel in an adaptor base screwed onto the vaporizer, and thereby to an indexed ISO key block connected to the fill bottle. Fluid thus flows from the bottle to the vaporizer and decompressing air flows back. For overfill protection, a special plug is fashioned to screw up into the existing sight glass access hole, and overfilling fluid flows from the vaporizer to the sight glass and then through the plug into the base where it exhausts. The sight glass continues to function accurately as a level indicator. During vaporizer use a block end plug covers the fill fluid, exhaust, and air decompression holes on the base, so there is no unwanted fluid escape.

17 Claims, 7 Drawing Sheets

KEY-FILL VAPORIZER ADAPTOR WITH OVERFILL PROTECTION

INTRODUCTION AND DESCRIPTION OF THE PRIOR ART

It will be understood with reference to the applicant's earlier U.S. patent (U.S. Pat. No. 4,883,049) that it is important to provide safer means for filling anesthetic vaporizers than the pour-fill models presently in wide use. The present application involves a further configuration for specific vaporizers, the Drager™ 19 and 19.1; or others that similarly have air-decompression access only through the sight glass.

The advantages of having standard key block access for filling and draining vaporizers has been detailed in the applicant's earlier patent; and in other patents such as Canadian patent #2,041,184 (Whitaker, 1991), and will not be further elaborated here. The principle problem being addressed in the present application is that in some pour-fill vaporizers, such as the Drager™ 19 and 19.1, there is only a single access hole provided in the front for fluid to enter. Decompressing air is allowed to bubble-up, or to exit from another pan of the vaporizer. In either case, in order to install an adapter for use with a closed bottle (key-index) system, it's necessary to devise an escape for return air to allow a fluid flow.

The present invention provides a novel and, as far as is known, completely unanticipated solution to this problem, which is to insert a special hollow screw and banjo collar up into an existing screw hole underneath the vaporizer. This is connected by double piping (air and fluid) to a main adaptor base fastened to the front of the vaporizer. Channels through the adaptor base connect these pipes to a standard ISO key-fill block. Thus fluid flows from the key block, through the adaptor base, through the banjo, around the screw, and into the vaporizer; and decompressing air flows in return through the hollow screw and banjo to the adaptor base, key block, and hence the fill bottle. To prevent overfilling, a third channel through the adaptor base connects the sight glass fluid to the exterior of the adaptor base, adjacent the key block insertion cavity. Any overfilling of the vaporizer forces fluid along this overfill channel and the fluid exhausts (signaling an overfill situation). During vaporizer use, this passage is sealed by a key block plug that also seals the air and fill fluid channels. Decompression of the overfill fluid is achieved through the vaporizer's existing air decompression channel communicating with the top of the sight glass.

The present invention allows all the advantages of having a specifically assigned refill key index—that is anesthetics are not inadvertently mixed or substituted—as well as allowing this on a specific vaporizer, which heretofore was unavailable due to its configuration. It also provides for important overfill protection.

DETAILED DESCRIPTION OF THE INVENTION

For this description, refer to the following diagrams, wherein like numerals refer to like parts.

Figure 1:
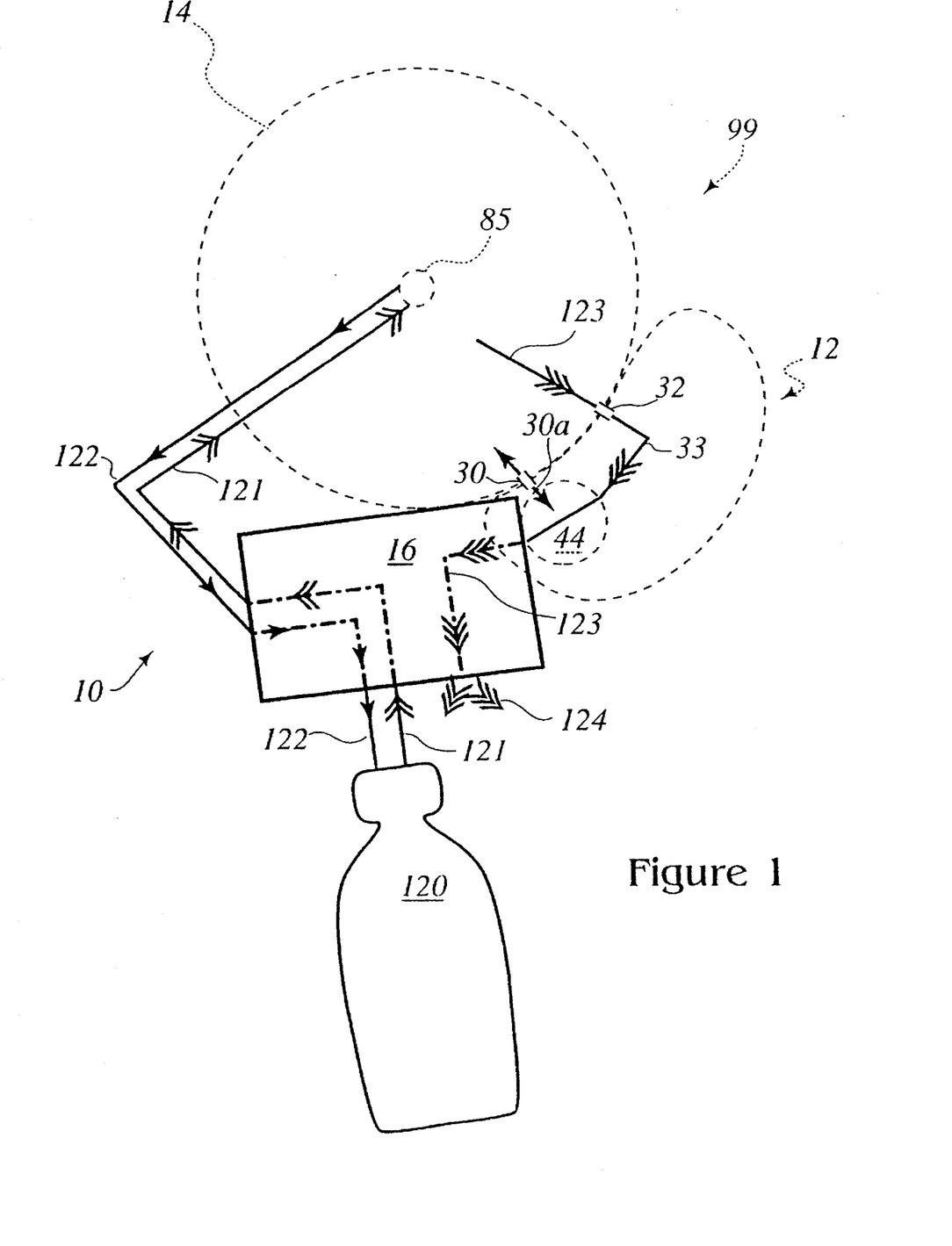
FIG. 1, schematic diagram of the fluid and air flow in the invented adaptor apparatus plan view.

Since the invention is a complex apparatus that can only be partially seen in any one figure due to the combination of pipes and channels through several bodies, it may help to give a quick theoretic overview before detailing the components. Turning to FIG. 1, which is a plan view schematic of air and liquid flow, the invented apparatus is generally indicated as 10 and the existing vaporizer is generally indicated as 99 (shown ghosted), including vaporizer body 14, fill apparatus generally indicated as 12 and sight glass 44.

As seen in simplified schematic FIG. 1, the invented fluid filling operates as follows: fill fluid (not shown) starts at bottle 120 and follows the path marked with double arrows 121 into and through the adaptor base 16 and then into vaporizer 14 by means of existing bottom screw hole 85 (shown ghosted). Decompressing air returns along a parallel path marked with single arrows 122, starting through hole 85 and proceeding through adaptor base 16 and into bottle 120. This allows the necessary filling and air decompression. If too much fill fluid is introduced, overfill fluid flows out of the vaporizer 14 along path indicated by triple arrows 123, first through existing vaporizer sight fluid channel 33, through sight glass 44, and then into and through the invented adaptor base 16, exhausting externally at radiating arrows 124, thereby signaling an overfill situation and venting the excess fluid. Note that the air decompression necessary to allow overfill fluid flow along path 123 is achieved through the existing air decompression channel 30a between the sight glass 44 and the vaporizer 14.

A key point being addressed is that the Drager™ models 19 and 19.1 have only a single air access hole 30 leading into sight glass 44, and a single front fluid access hole 32 communicating with integral existing fill apparatus 12. However the Drager™ also has threaded bottom screw hole 85, which can be better seen by turning to FIG. 5 where screw hole 85 can be seen to pass through vaporizer storage compartment 89. Thus the invention principally resides in providing for fluid flow into, and decompressing air flow out of, this screw hole 85, by means of special hollow screw generally indicated as 79 on FIG. 5.

Elements of the illustrated embodiment will now be described in fuller detail. The invented adaptor 10 is generally indicated on FIG. 2, where adaptor base 16 is illustrated in usage position fastened to fill apparatus 12. The vaporizer 14 can be assumed to be a Drager™ model 19 or 19.1, or other having a fill apparatus 12 functionally identical to these Drager™ models.

Figure 2:
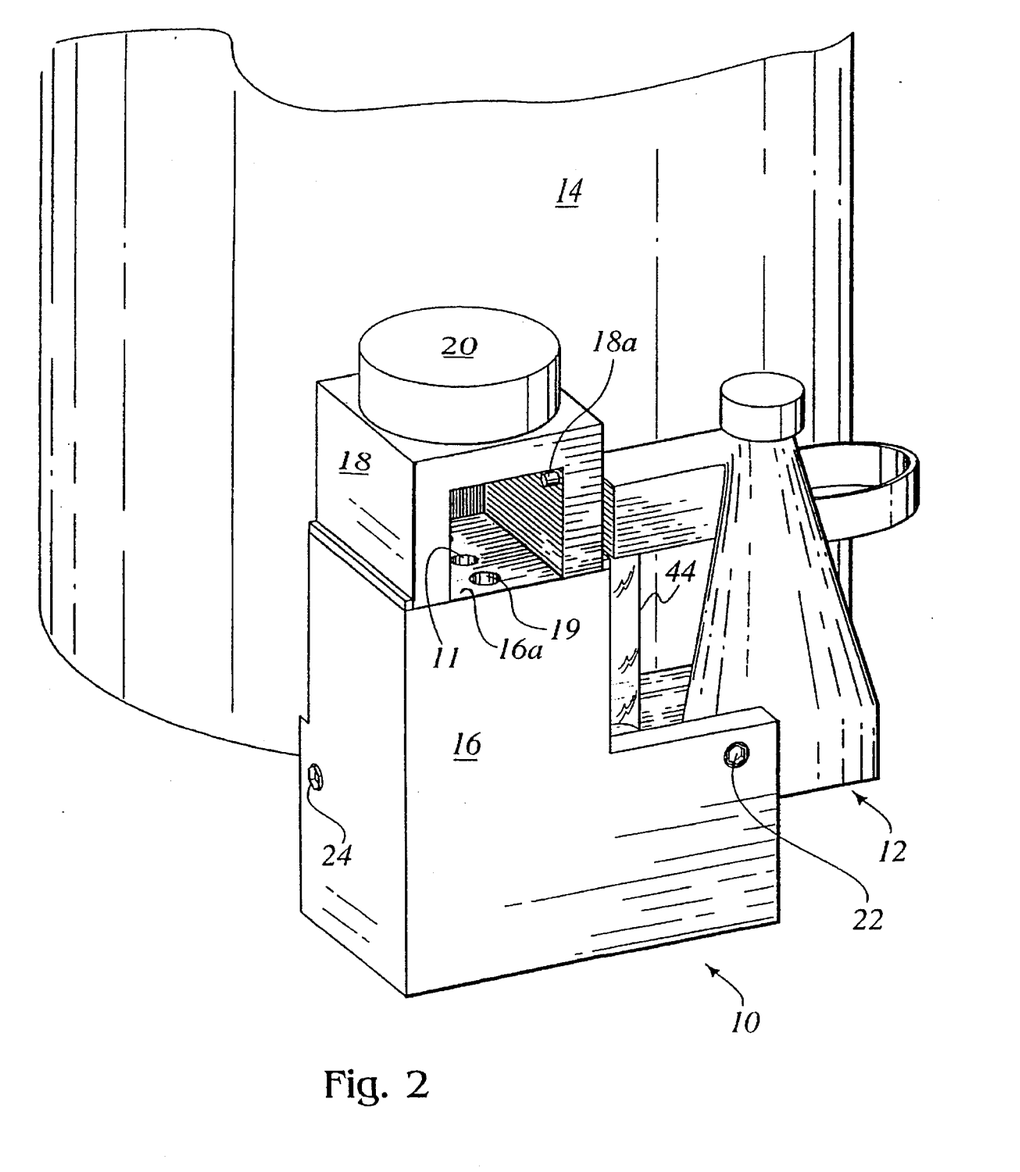
FIG. 2, the invented adaptor showing adaptor base in usage position; front perspective view.
Figure 3:
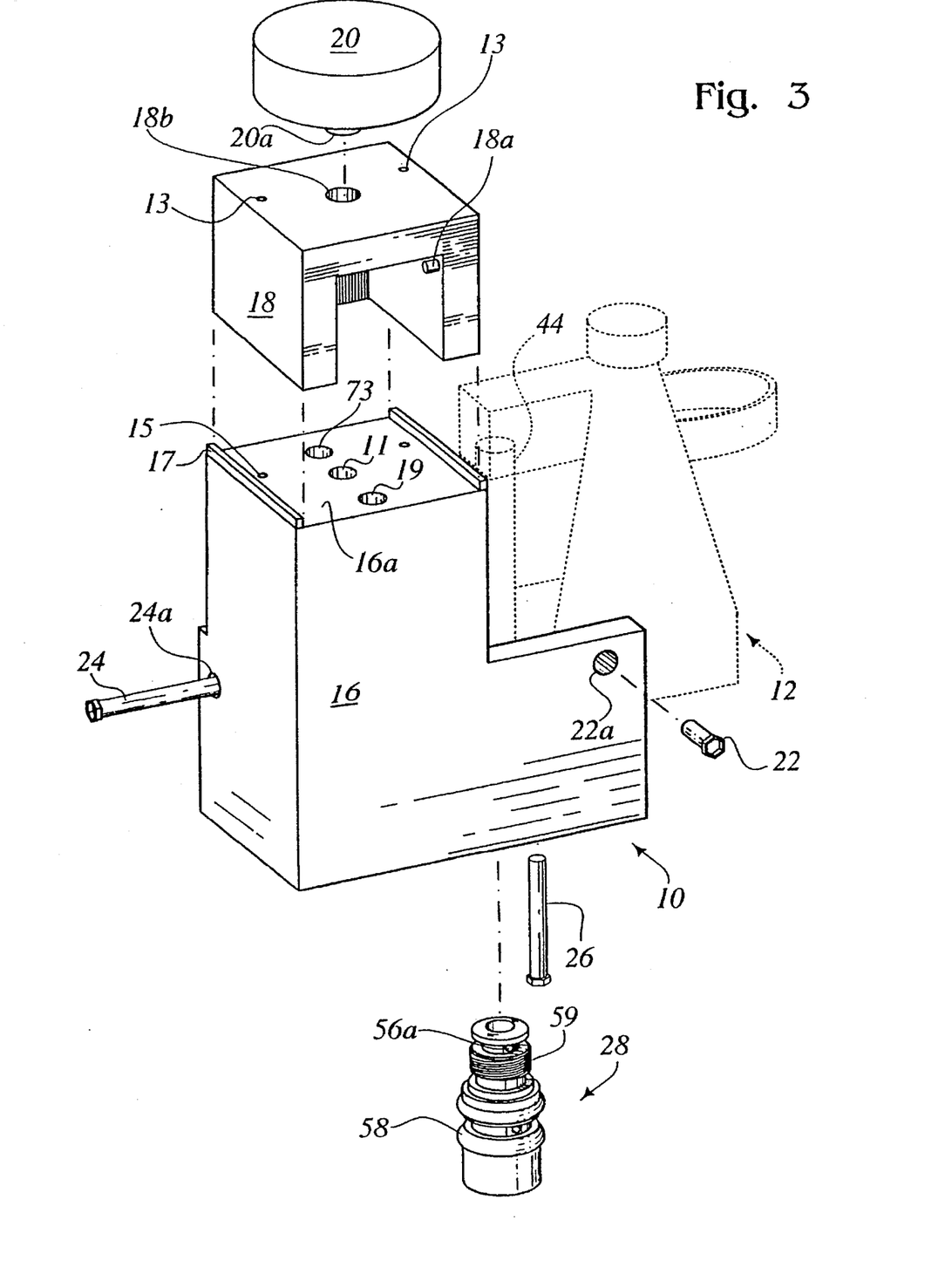
FIG. 3, the adaptor base of FIG. 2; exploded front perspective view.

In FIG. 3 the elements of adaptor base 16 visible in FIG. 2 are exploded to additionally show indexed overpass 18 with index pin 18a, knob hole 18b and screw holes 13; overpass knob 20 with overpass knob pin 20a; and set screws 22, 24, and 26 with corresponding set screw holes 22a, 24a, and 26a (26a is not shown). On FIG. 3 can also be seen that base 16 has lips 17 for aligning overpass 18 against base top surface 16a, screw holes 15 corresponding to screw holes 13 in overpass 18 for fastening overpass 18 to base top surface 16a (screws not shown), and base air channel exhaust port 11, base fluid channel intake port 19, and base overfill exhaust port 73.

Figure 4A:
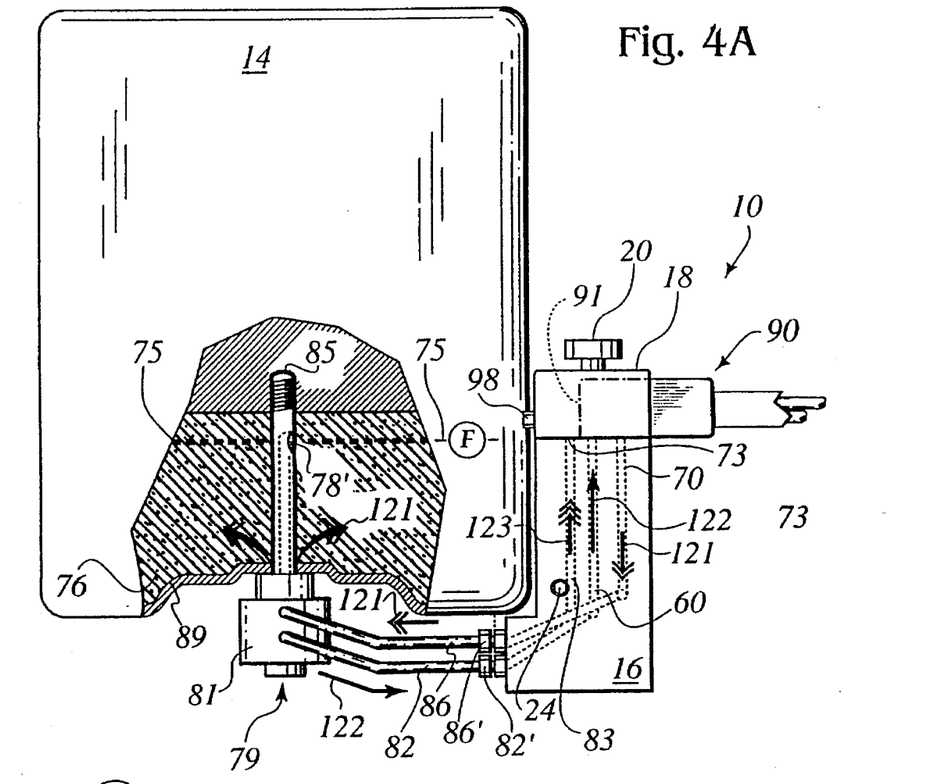
FIG. 4A, an invented adaptor of FIG. 2, except with key block inserted; partial cut-away side view.
Figure 4B:
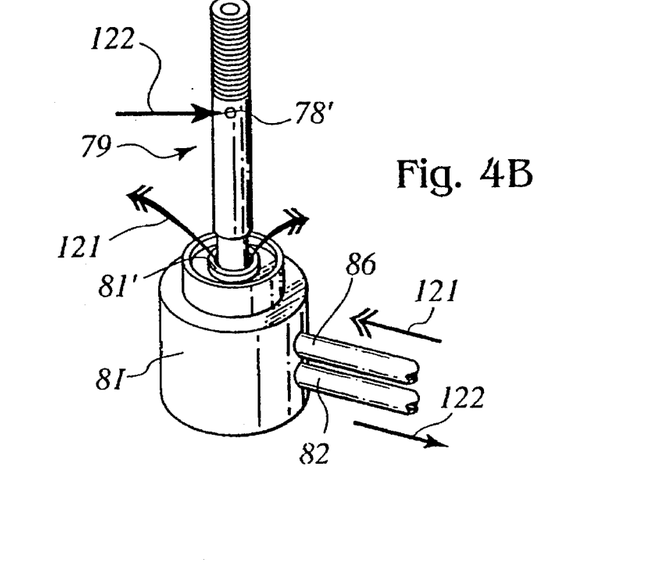
FIG. 4B, detail of FIG. 4A, perspective view.
Figure 5:
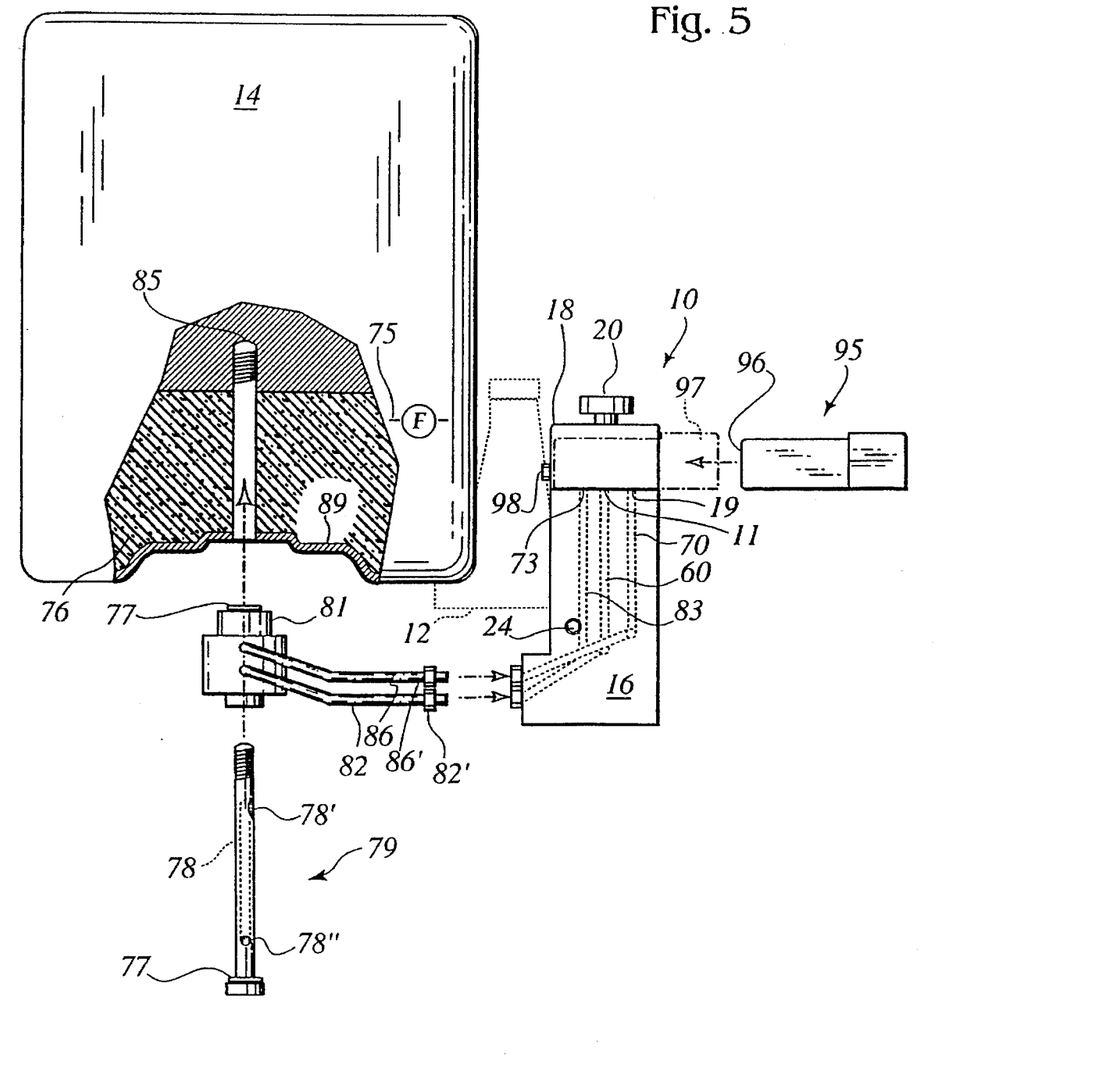
FIG. 5, the adaptor of FIG. 4A except with key block plug; exploded partial cut-away side view.

On FIG. 4A, along with perspective detail FIG. 4B and exploded view FIG. 5, can be seen the elements of the adaptor 10 not visible in FIGS. 2 and 3. Most importantly these elements are hollow retaining screw 79, banjo 81 (held in place by screw 79), air decompression pipe 82, and fill pipe 86. Retaining screw air intake port 78' is shown; and in FIG. 5 only, retaining screw exhaust port 78" and hollow passage 78 are shown (hollow passage 78 is shown ghosted).

Figure 6:
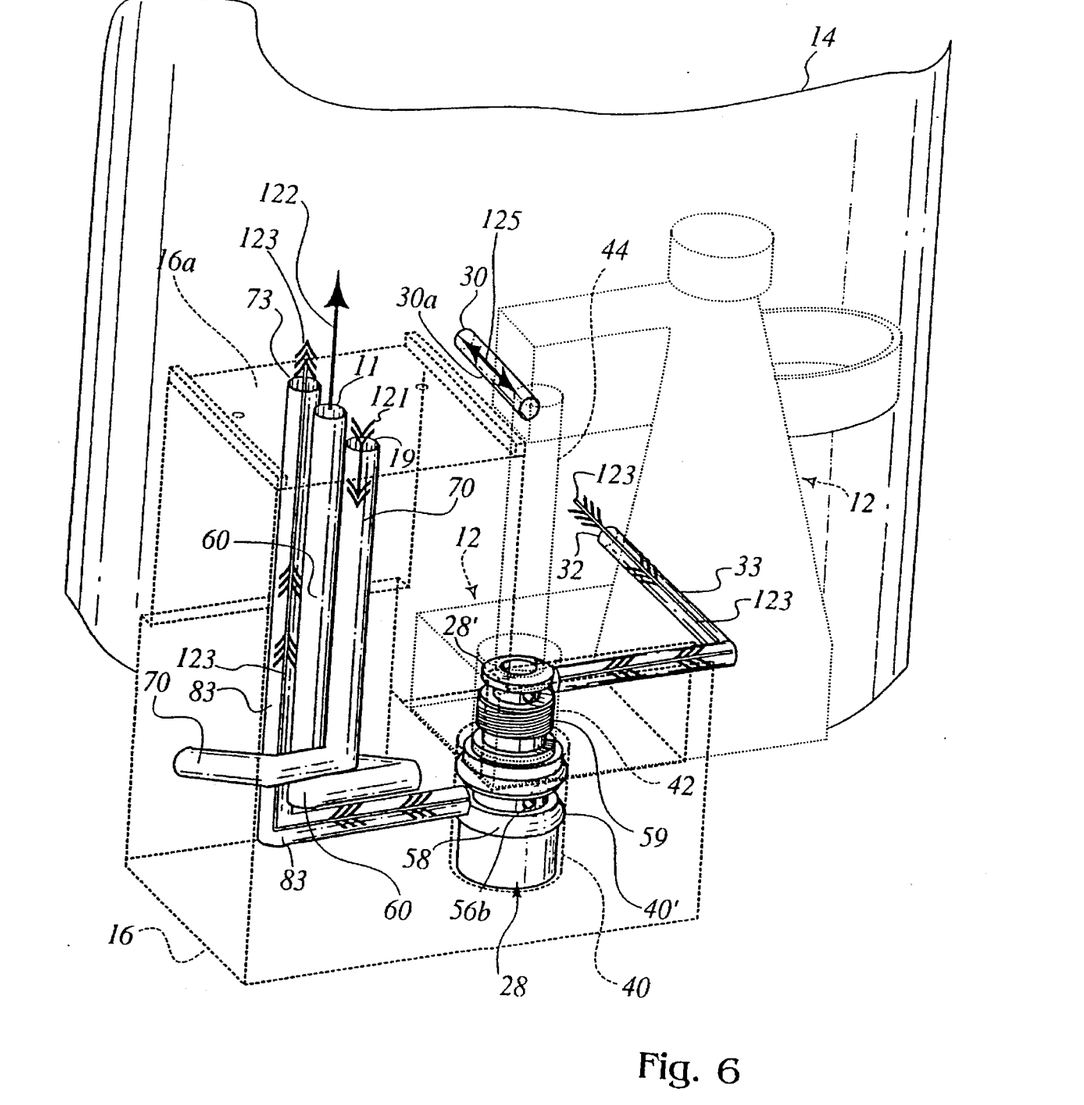
FIG. 6, the adaptor base of FIG. 2, showing air and fluid flow channels from key block to vaporizer; partially ghosted perspective view.

Base fluid channel 70 and base air channel 60 can be seen ghosted on FIGS. 4A and 5, but are more fully shown in FIG. 6 inside ghosted base 16, where can also be seen overfill channel 83.

Sight glass screw plug generally indicated as 28 is shown in FIG. 3, but is perhaps better appreciated in FIG. 6 where it is shown in its functioning position inside ghosted base 16 and extending up into ghosted fill apparatus 12. Screw plug 28 has been inserted through bore hole 40 especially fashioned in base 16 and therethrough into sight access hole 42 pre-existing in fill apparatus 12.

Figure 7:
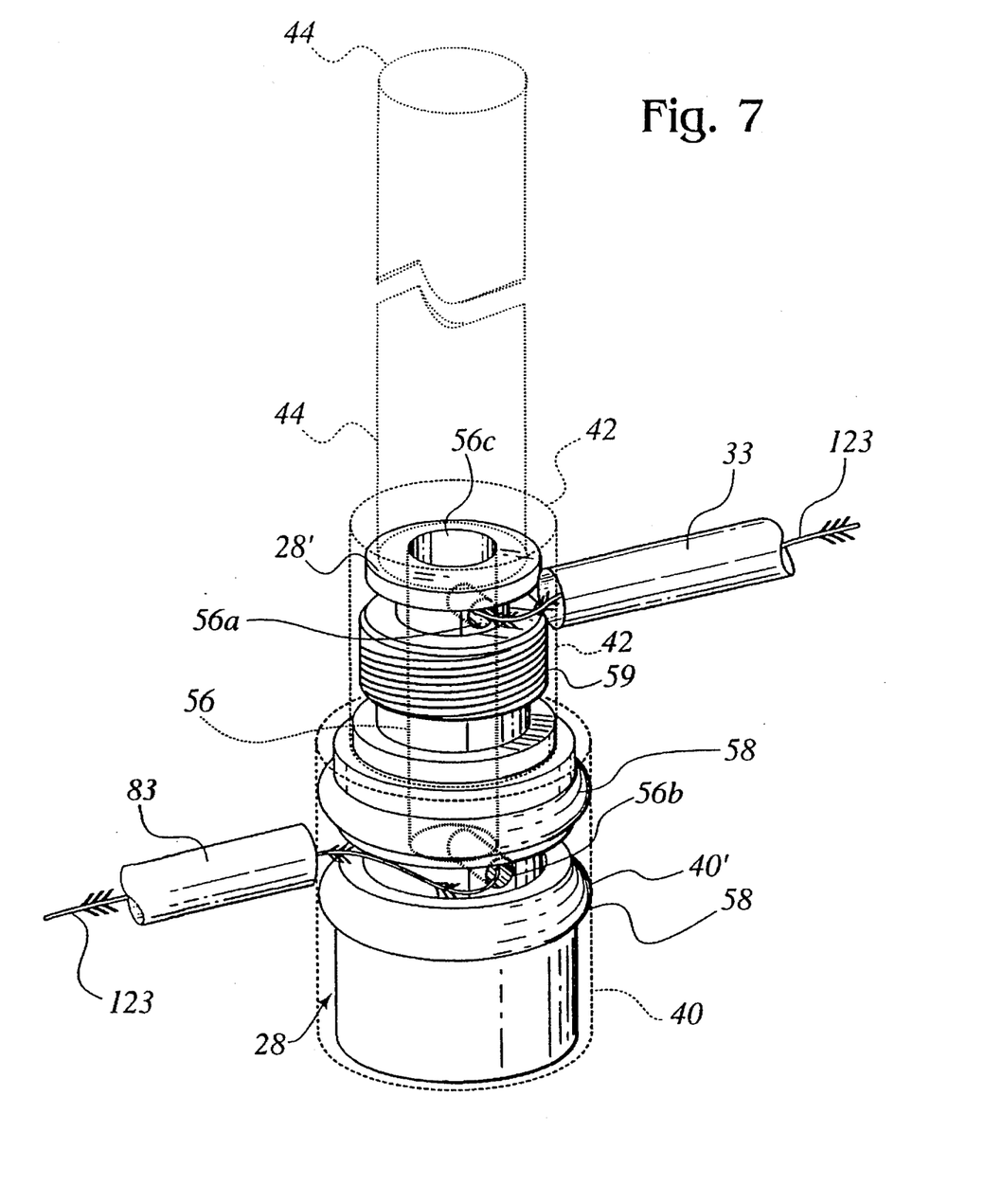
FIG. 7, detail of FIG. 6 showing air and fluid channels through the screw plug; partially ghosted perspective view.

Screw plug 28 is shown enlarged in FIG. 7. A plug channel 56 shown ghosted, runs from plug intake port 56a to plug exhaust port 56b, and opens also at plug channel mouth 56c into sight glass 44 (shown ghosted resting on top surface 28' of plug 28). O-rings 58 on plug 28 prevent fluid leakage (fluid not shown) from bore hole 40 by contacting bore hole 40 concentrically, such as at point 40'. Thread 59 mates with corresponding pre-existing thread inside sight glass access hole 42 (thread of the access hole 42 is not shown).

The invention is assembled for operation as follows: in FIG. 2 can be seen base 16 fixed in position onto vaporizer fill apparatus 12 by means of set screws 22, 24. and 26 (screw 26 is visible in exploded view FIG. 3). With reference to FIGS. 3, 6 and 7, screw plug 28 will be understood to be inserted through bore hole 40 in base 16 (bore hole 40 is shown ghosted in FIGS. 6 and 7) and thence into sight glass access hole 42 (also ghosted) in vaporizer fill apparatus 2 (not shown in FIG. 7). Plug thread 59 mates with existing thread (not shown) in:side sight glass access hole 42, so that screw plug 28 is screwed firmly into position with sight glass 44 (shown ghosted) resting on top surface 28' of screw plug 28.

Hollow retaining screw 79, shown in exploded view in FIG. 5, is inserted through banjo 81 into position shown in FIG. 4B and then screwed into position shown in FIG. 4A, into existing screw hole 85 in vaporizer 14. Air pipe 82 and fluid pipe 86, both integral with banjo 81, are coupled to adaptor 16 by means of coupling 82' and coupling 86' respectively.

Finally, ISO standard key block generally indicated as 90 in FIG. 4A is inserted to the position shown; note that end 91 of key block 90, shown ghosted inside overpass 18, does not reach as far as overfill exhaust port 73. As is standard with key blocks such as 90, note on FIG. 3 how the entry of such a block (not shown) will be allowed only for a particular vapor fluid that corresponds to color coding on the overpass knob 20 and the position of the index pin 18a (color coding is not shown). In other words, the correct key block (not shown in FIG. 3) will have an air channel that will position over base air exhaust port 11, a fluid channel that will simultaneously position over base fluid intake port 19, and an index pin cavity that will mate with index pin 18a. (Again, such a key block 90 is shown in FIG. 4A, but channels and index pin cavity inside key block 90 are not shown).

The invention operates as follows: probably best understood principally with reference to FIG. 4A, filling of the vaporizer 14 is accomplished as fluid travels from bottle 120 (shown on FIG. 1), through ISO standard key block 90 (to return to FIG. 4A), along base fill fluid channel 70 in direction of double arrows 121, through fluid pipe coupling 86', inside fluid pipe 86, through banjo 81 by means of a short fluid channel (not shown) inside banjo 81, and into vaporizer 14 by following the path of double arrows 121 on FIG. 4B, flowing between collar 81' and screw 79. Thereupon the fluid is absorbed by absorbent area 76 shown on FIGS. 4A and 5. Meanwhile, to achieve this flow, decompressing air flows in return entering first intake port 78', and then passing through hollow passage 78 and screw exhaust port 78" (these last two shown on FIG. 5 only), through a short banjo air channel (not shown) connecting with screw exhaust port 78", and then (returning to FIG. 4A) along air pipe 82, through air pipe coupling 82', through adaptor base 16 by means of base air channel 60 in direction of arrow 122, and therethrough into ISO standard key block 90 and then on into bottle 120 shown in FIG. 1. Banjo O-rings 77 shown on FIG. 5 ensure the tight sealing of banjo 81 against vaporizer 14 and hollow retaining screw 79 against banjo 81. Hollow retaining screw 79 holds banjo 81 in place.

The overfill protection operates as follows: in some vaporizers, such as the Drager™ 19 and 19.1, it is inadvisable to fill past a certain level; in FIG. 4A this maximum advisable fill level 75 is represented by the two horizontal lines on either side of the "F" and is also indicated inside the vaporizer with a heavy dotted horizontal line. When absorbent area 76 has been filled to maximum level 75, overfill fluid, represented by triple arrows 123 in FIG. 6 (and seen also on FIG. 1), travels along existing sight glass fluid channel 33, through screw plug 28, overfill channel 83, and out overfill exhaust port 73. How the overfill fluid travels through screw plug 28 is best understood with reference to FIG. 7, where overfill fluid represented by triple arrows 123 can be seen entering plug intake port 56a; travels vertically down through plug channel 56 (shown ghosted); and can be seen exiting through plug exhaust 56b and entering overfill channel 83, again indicated as triple arrows 123.

Note that sight glass 44 still fills with fluid and functions as an accurate sight glass (fluid not shown), since fluid enters inside sight glass 44 by means of plug channel mouth 56c, and, with reference to FIG. 6, decompressing air enters and exits from sight glass 44 through decompression channel 30a as indicated by opposing arrowheads 125.

To return to the overfilling system with reference to FIG. 4A, key block generally indicated as 90 has end 91 (ghosted) that does not reach as far as overfill channel exhaust port 73, thus allowing any overfill fluid moving in direction of arrow 123 to exhaust through port 73 (this exhausting is not shown in FIG. 4A). Overfilling fluid exiting through exhaust port 73 can further exhaust through escape port 98 (shown in FIGS. 4A and 5) in overpass 18, which will indicate that overfilling is occurring. (Such exit is not shown). A collection vessel may be attached to escape port 98 to prevent escape into the air. (Such collection is not shown).

After filling is completed, a key block plug generally indicated as 95 is shown in FIG. 5 having end 96 which, when key block plug 95 is in ghosted position 97, covers exhaust port 73 and prevents fluid flow (as well as covering and sealing air exhaust port 11 and fluid intake port 19.)

Thus a vaporizer 14 such as the Drager™ 19 and 19.1 illustrated in these figures is filled using the invented adaptor 10 shown, using a closed key-fill system with standard key blocks. An overfill protection system is included so that filling past a maximum fill level is avoided.

The foregoing is by example only, and the scope of the invention should be limited only by the appended claims.

The embodiments of the Invention in which an exclusive property or privilege is claimed are defined as follows:

1. In a pour-fill anaesthetic vaporizer having a storage compartment screw hole and a sight glass, an adaptor apparatus that converts said vaporizer into a key-fill vaporizer with overfill protection; said apparatus comprising: fill fluid channeling means from an ISO standard key block through the storage compartment screw hole; decompressing air channeling means through said storage screw hole to the key block; and overfill fluid channeling means from the sight glass;

whereby the vaporizer may be filled by feeding fluid with positive pressure into the key block, and hence through the fill fluid channeling means and into the vaporizer; while simultaneously decompressing air flows from the vaporizer and into the key block; and whereby any overfilling fluid flows from the sight glass and escapes, thereby signaling overfill.

2. An apparatus as in claim 1, in which the vaporizer is configured identically to the Drager™ model 19, and the storage compartment screw hole is an existing screw hole in the bottom of the vaporizer.

3. An apparatus as in claim 1, in which the vaporizer is chosen from the group consisting of: Drager™ model 19; Drager™ model 19.1; and a vaporizer configured substantially identically to the Drager™ model 19; and further in which the storage compartment screw hole is an existing screw hole in the bottom of the vaporizer.

4. An apparatus as in claim 1, in which the fill fluid channeling means partially comprises a cavity between a retaining screw extending through the storage screw hole and a collar encircling the retaining screw, and the decompressing air channeling means partially comprises a longitudinal hollow through the screw.

5. An apparatus as in claim 4, in which the vaporizer is chosen from the group consisting of: Drager™ model 19; Dager™ model 19.1; and a vaporizer configured substantially identically to the Drager™ model 19; and further in which the storage screw hole is an existing screw hole in the bottom of the vaporizer.

6. An apparatus as in claim 5, in which the overfill fluid channeling means partially comprises a channel in a screw plug screwed into existing screw threads in an existing sight glass access hole in the vaporizer.

7. An apparatus as in claim 6, in which the channel in the screw plug also communicates with the sight glass, so that the sight glass continues to function as an accurate fluid level indicator.

8. In a pour-fill anaesthetic vaporizer chosen from the group consisting of: Drager™ model 19; Drager™ model 19.1; and a vaporizer configured substantially identically to the Drager™ model 19: an adaptor apparatus that converts said pour-fill vaporizer into a key-fill vaporizer with overfill protection; said apparatus comprising:

a base body, comprising:
      a bore hole for a screw plug;
      a base air channel;
      a base fill fluid channel;
      a base overfill fluid channel; and
      means of fastening the base to the vaporizer;
   a screw plug, comprising:
      a partially threaded plug body configured to mate with existing thread in the existing sight glass access hole in the vaporizer; and
      a plug channel through the plug body configured to communicate between the existing sight glass fluid channel in the vaporizer and the base overfill fluid channel;
   a retaining screw threaded into existing screw thread in the existing storage compartment screw hole in the vaporizer;
   an air hole running lengthwise through the retaining screw;
   a banjo encircling the retaining screw exterior to the vaporizer; said banjo comprising:
      a banjo fluid channel communicating with the interior of the vaporizer;
      a fluid pipe communicating from the banjo fluid channel to the base fill fluid channel;
      a banjo air channel communicating with the air hole through the retaining screw; and
      a banjo air pipe communicating from the banjo air channel to the base air channel; and
   means of fastening an ISO standard key block on the base so that the fluid channel of the key block communicates with the base fill fluid channel and the air channel of the key block communicates with the base air channel;
   whereby a person may fill such a vaporizer by fastening said key block on the base using said fastening means and raising a refill bottle communicating with the key block; so that fluid flows frown the bottle through the key block base fill fluid channel, fluid pipe, and banjo fluid channel and into the vaporizer, and decompressing air flows from the vaporizer, through the retaining screw air hole, banjo air channel, air pipe, base air channel, and into the key block and hence bottle;
   and wherein overfilling fluid will exhaust through the sight glass, screw plug, and base overfill fluid channel, and hence signal overfilling.

9. An apparatus as in claim 8, in which the means of fastening the key block on the base comprises an overpass that the key block fits into; and further in which the base overfill fluid channel exhausts into a space between the key block and the overpass.

10. An apparatus as in claim 8, in which the key block fastening means is indexed and will only accept a reciprocally indexed key block.

11. An apparatus as in claim 9, in which the overpass is indexed and will only accept a reciprocally indexed key block.

12. An apparatus as in claim 9, in which an escape port through the overpass allows the overfilling fluid to exit from said space.

13. An apparatus as in claim 9, in which removable overfill channel sealing means allows escape of liquid through the overfill passage during vaporizer filling periods and prevents such escape during non-filling periods.

14. An apparatus as in claim 13, in which the channel sealing means comprises a key block plug inserted into the overpass when the vaporizer is not being filled.

15. An apparatus as in claim 14, in which there is an overpass knob on top of the overpass and an overpass pin through the overpass, by which a key block may be firmly fixed in position.

16. In a pour-fill anesthetic vaporizer chosen from the group consisting of: Drager™ model 19; Drager™ model 19.1; and a vaporizer configured substantially identically to the Drager™ model 19: an adaptor apparatus that converts said pour-fill vaporizer into a key-fill vaporizer with overfill protection; said pour-fill anesthetic vaporizer partially comprising the elements: sight glass, threaded sight glass access hole; sight glass fluid channel; sight glass air decompression channel; and threaded storage compartment screw hole; and said apparatus comprising:

a base body, comprising:
  a bore hole for a screw plug;
  a base air channel;
  a base fill fluid channel;
  a base overfill fluid channel; and
  set screws configured for fastening the base to the vaporizer;
 a screw plug, comprising:
  a partially threaded plug body configured to mate with the thread in the vaporizer sight glass access hole; and
  a plug channel through the plug body configured to communicate between the sight glass fluid channel and the base overfill fluid channel;
 a retaining screw threaded into the storage compartment screw hole;
 an air hole running lengthwise through the retaining screw;
 a banjo encircling the retaining screw exterior to the vaporizer; said banjo comprising:
  a banjo fluid channel communicating with the interior of the vaporizer;
  a fluid pipe communicating from the banjo fluid channel to the base fill fluid channel;
  a banjo air channel communicating with the air hole running through the retaining screw; and
  an air pipe communicating from the banjo air channel to the base air channel;
 a removable overpass configured to allow indexed fastening of a reciprocally indexed ISO standard key block on the base so that: the fluid channel of the key block communicates with the base fill fluid channel; the air channel of the key block communicates with the base air channel; and the overfill fluid channel exhausts into a space between the key block and the overpass;
 an escape port through the overpass communicating with said space between the key block and the overpass; and
 a key block plug fashioned to be inserted into the overpass instead of the key block when the vaporizer is not being filled;
 whereby a person may fill such a vaporizer by inserting an indexed key block into the overpass and providing positive fluid pressure from a refill bottle communicating with the key block; so that fluid flows from the bottle through the key block, base fill fluid channel, fluid pipe, and banjo fluid channel into the vaporizer, and decompressing air flows from the vaporizer, through the retaining screw, banjo air channel, air pipe, base air channel, and into the key block and hence refill bottle;
 wherein overfilling fluid will exhaust through the sight glass fluid channel, sight glass, screw plug channel, base overfill fluid channel, and escape port, and hence signal overfilling; and
 wherein when the vaporizer is not being filled a key block plug is inserted into the overpass and seals the base fill fluid channel, the base air decompression channel, and the base overfill fluid channel, and prevents unwanted escape of fluid.

17. An adaptor as in claim 16, in which the banjo fluid channel partially comprises a cavity between the outer surface of the retaining screw and a collar encircling the retaining screw; said collar being integral with the banjo.

* * * * *